(12) United States Patent
Levine et al.

(10) Patent No.: US 9,271,638 B2
(45) Date of Patent: Mar. 1, 2016

(54) DENTAL RETRACTOR FOR USE IN TEETH WHITENING

(71) Applicant: JBL Radical Innovations, LLC, New York, NY (US)

(72) Inventors: Jonathan B. Levine, Purchase, NY (US); Elmar A. Dave, Clifton, NJ (US)

(73) Assignee: JBL RADICAL INNOVATIONS, LLC

( * ) Notice: Subject to any disclaimer, the term of this patent is extended or adjusted under 35 U.S.C. 154(b) by 0 days.

(21) Appl. No.: 14/027,579

(22) Filed: Sep. 16, 2013

(65) Prior Publication Data

US 2015/0079541 A1 Mar. 19, 2015

(51) Int. Cl.
*A61C 5/00* (2006.01)
*A61B 1/24* (2006.01)
*A61C 5/14* (2006.01)
*A61C 19/06* (2006.01)

(52) U.S. Cl.
CPC ... *A61B 1/24* (2013.01); *A61C 5/14* (2013.01); *A61C 19/066* (2013.01)

(58) Field of Classification Search
CPC ............... A61B 1/24; A61C 5/12; A61C 5/14
USPC .............. 433/91, 93, 136–141; 600/235–239, 600/206, 208, 210, 216; 128/859, 862
See application file for complete search history.

(56) References Cited

U.S. PATENT DOCUMENTS

| | | | |
|---|---|---|---|
| 4,511,329 A * | 4/1985 | Diamond | 433/31 |
| 6,322,362 B1 * | 11/2001 | Holms | 433/143 |
| 6,923,761 B1 * | 8/2005 | Dorfman | 600/237 |
| D617,455 S * | 6/2010 | Mori et al. | D24/135 |
| 2007/0148619 A1* | 6/2007 | Anderson | 433/136 |

* cited by examiner

*Primary Examiner* — Heidi M Eide
(74) *Attorney, Agent, or Firm* — H. Jay Spiegel

(57) ABSTRACT

The inventive retractor includes two half-moon shaped trays at each side located on the sides of the mouth covering the lips and opening the mouth to reveal the teeth from the front. The trays are interconnected by a strap-like member spacing the upper and lower teeth from one another by a slight amount. The angulation between the trays and the strap-like member is devised to improve the patient's comfort level and to better facilitate alignment of the retractor with typical human oral anatomy. Each of the inventive trays has a handle so that the retractor may easily be gripped for insertion into the mouth and removal therefrom.

20 Claims, 3 Drawing Sheets

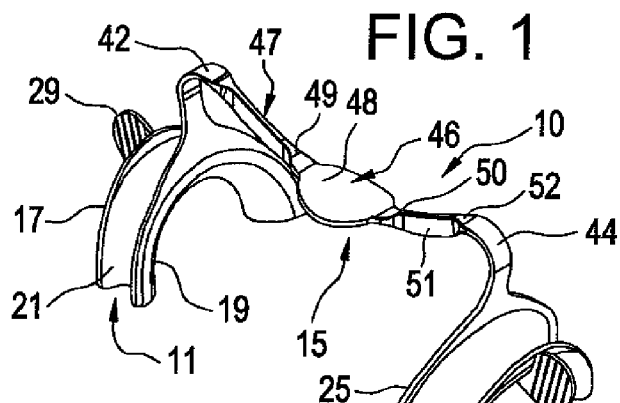
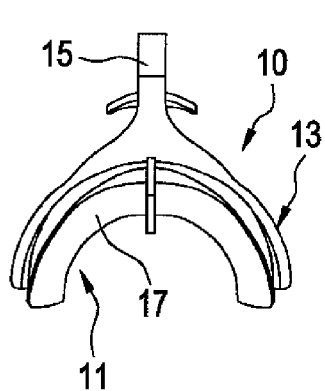
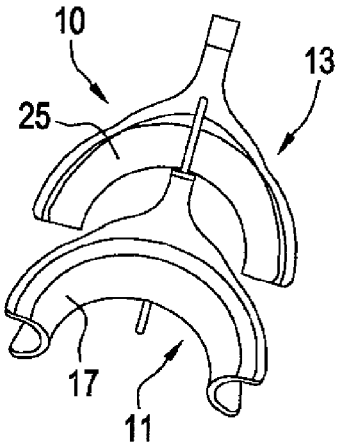
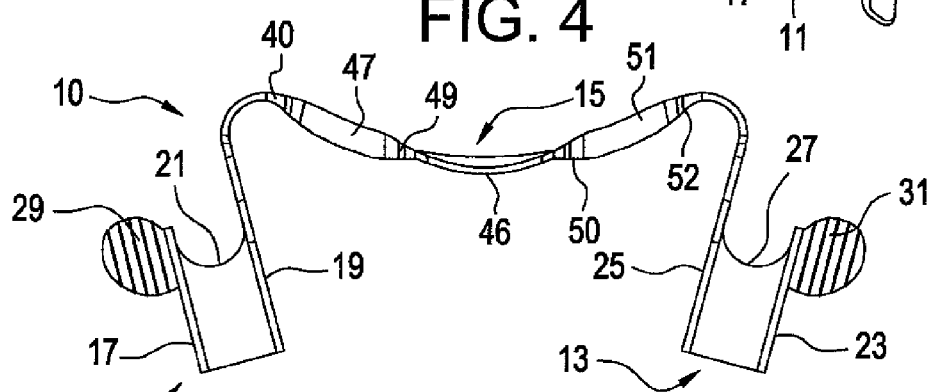
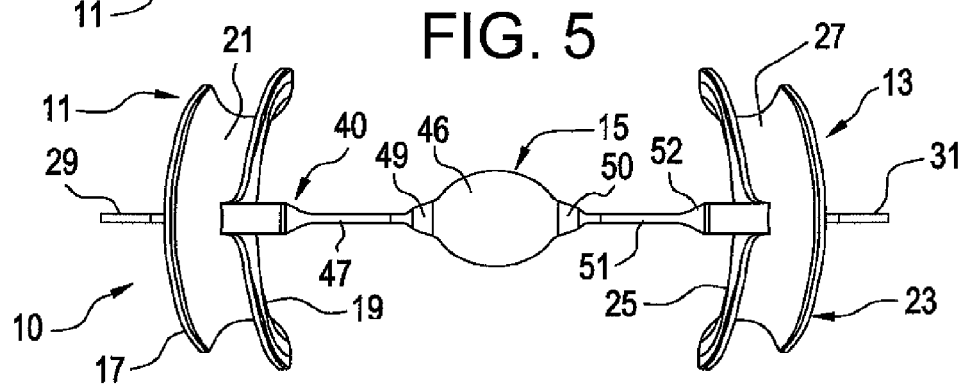

DENTAL RETRACTOR FOR USE IN TEETH WHITENING

BACKGROUND OF THE INVENTION

The present invention relates to a dental retractor for use in teeth whitening. The teeth whitening industry has grown by leaps and bounds in recent years. One preferred method of whitening teeth involves the use of a mouthpiece inserted in the mouth and enclosing a teeth whitening substance such as a concentration of hydrogen peroxide. Often, in practicing teeth whitening using a mouthpiece, it is advantageous to first coat the teeth with a teeth whitening composition and then insert the mouthpiece to seal the teeth whitening substance in place on the tooth surfaces.

It is known that some teeth whitening substances can be irritating to the gums and lips of a patient if the substances coat the surfaces of those body parts. As such, it is also advantageous to find a way to best preclude the teeth whitening substance from inadvertently coating the lips and gums of the patient or user. A retractor which acts to space the lips from the teeth and renders the gums clearly visible to allow the patient, user or their dentist to "paint" the teeth whitening substance onto tooth surfaces without the substance coating the lips and gums would be an advantageous device to employ in this context. It is with this thought in mind that the present invention was developed.

SUMMARY OF THE INVENTION

The present invention relates to a dental retractor for use in teeth whitening. The present invention includes the following interrelated objects, aspects and features:

(1) In a first aspect, the inventive retractor includes two half-moon shaped trays at each side that are designed to be located on the sides of the mouth covering the lips and opening the mouth to reveal the teeth from the front.

(2) These trays are interconnected by a strap-like member. The strap-like member acts to space the upper and lower teeth from one another by a slight amount.

(3) The angulation between the trays and the strap-like member is specifically devised to improve the patient's comfort level and to better facilitate alignment of the retractor with typical human oral anatomy.

(4) Each of the inventive trays has integrally formed therewith a handle so that the retractor may easily be gripped for insertion into the mouth and removal therefrom. Each handle has integrally formed therewith an anti-slip surface such as a series of parallel ribs to maximize gripability.

(5) In the preferred embodiment of the present invention, the inventive retractor is made of a soft plastic, rubber or synthetic rubber material to facilitate connection of the strap-like member and to enhance the comfort level of the patient/user when the retractor is inserted, retained in the mouth of the user, and removed therefrom.

(6) In the preferred embodiment, once the retractor has been installed into the mouth of the user, a teeth whitening composition may be painted or otherwise coated onto the tooth surfaces of the patient's teeth, whereupon a specially designed mouthpiece may be inserted into the mouth of the user with the retractor in place. Such a mouthpiece may, if desired, include sealing features that facilitate sealing the teeth whitening composition from exposure to the atmosphere to therefore enhance retention on the tooth surfaces of the oxygen molecules that have the purpose of whitening the teeth.

As such, it is a first object of the present invention to provide a dental retractor for use in teeth whitening.

It is a further object of the present invention to provide such a retractor in which two half-moon shaped trays are interconnected by a strap-like member.

It is a still further object of the present invention that the strap-like member is intended to space the upper and lower teeth from one another by a slight distance.

It is a still further object of the present invention to provide such a retractor in which handles are incorporated into the opposed trays to best facilitate installation and removal.

It is a still further object of the present invention that the inventive retractor be made of a flexible material to enhance insertion and removal as well as to reduce any discomfort to the patient.

These and other objects, aspects and features of the present invention will be better understood from the following detailed description of the preferred embodiment when read in conjunction with the appended drawing figures.

BRIEF DESCRIPTION OF THE DRAWINGS

FIG. 1 shows a perspective view of the present invention.

FIG. 2 shows a side view of the present invention.

FIG. 3 shows a further perspective view slightly rotated from the view of FIG. 2.

FIG. 4 shows a front view of the present invention.

FIG. 5 shows a top view of the present invention.

SPECIFIC DESCRIPTION OF THE PREFERRED EMBODIMENT

Figure 11:
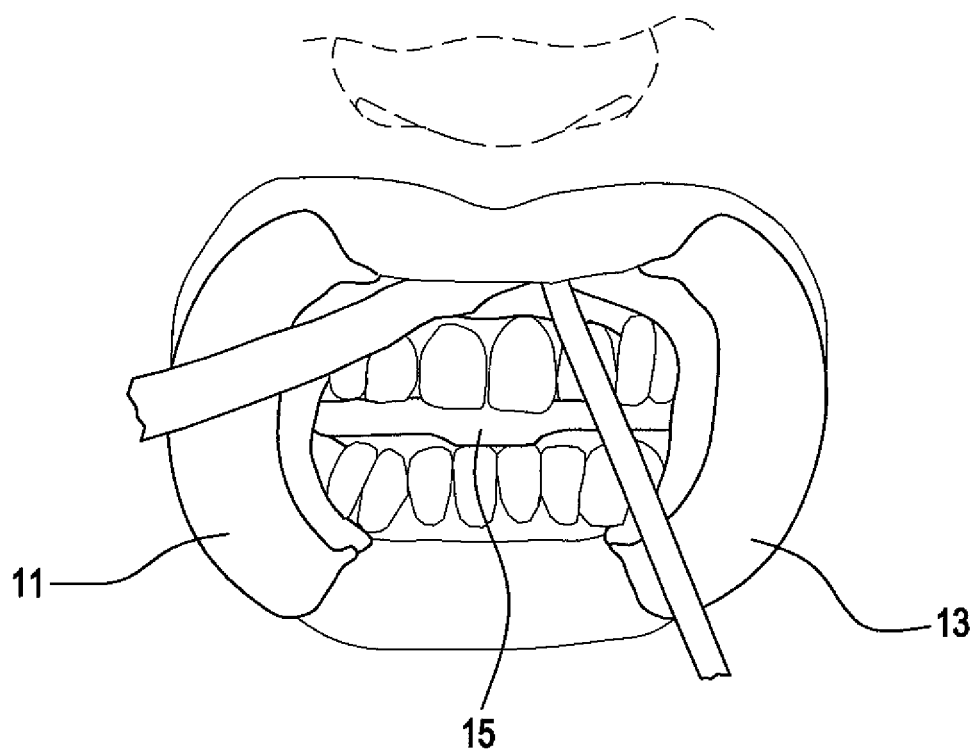
FIG. 11 shows a front view of the inventive retractor as installed in the mouth of a user.

With reference to FIGS. 1-6, the inventive dental retractor is generally designated by the reference numeral 10 and includes half-moon shaped arcuate trays 11 and 13 interconnected by a strap-like member 15. The tray 11 includes side walls 17 and 19 which define therebetween a surface 21 which is arcuate both laterally and in the anterior-posterior direction. Similarly, the tray 13 includes side walls 23 and 25 that define therebetween a surface 27 that is arcuate both laterally and in the anterior-posterior direction. As best seen in FIG. 11, the trays 11 and 13 are designed to overlie interiorly and exteriorly the side portions of the lips of the user including intersecting portions of a user's upper and lower lips and maintain the mouth slightly open with the teeth exposed.

Figures 9, 10:
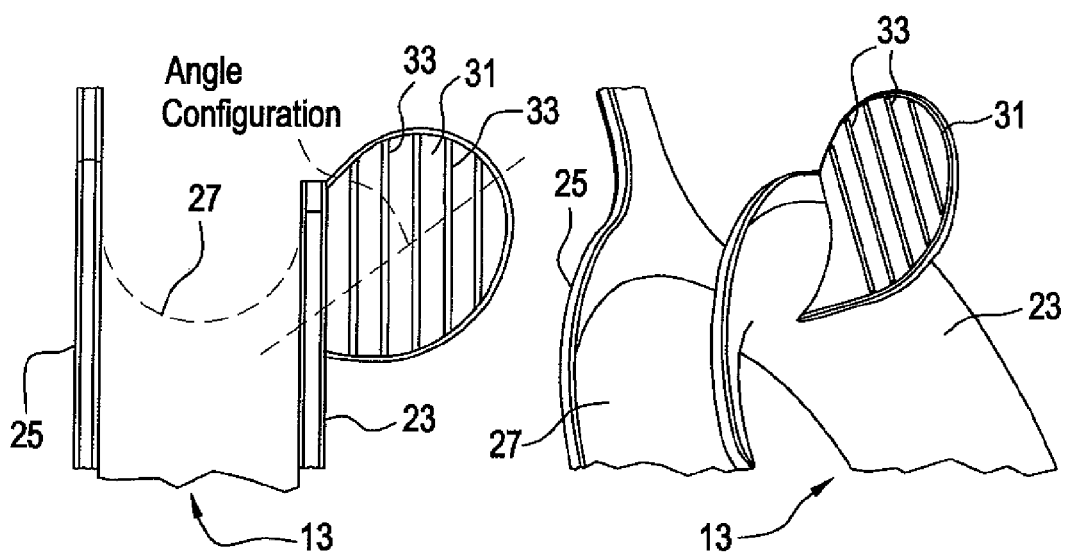
FIG. 9 shows a close-up front view of one of the handles of the present invention.
FIG. 10 shows a perspective view of one of the handles of the present invention as attached to one of the trays.

The tray 11 includes an integrally formed handle 29 while the tray 13 includes an integrally formed handle 31. The handles 29 and 31 comprise flat tabs. With reference to FIGS. 9 and 10, a close-up of a portion of the tray 13 is shown and the handle 31 is seen to include an anti-slip gripping surface consisting of a plurality of parallel ribs 33 which enhance the grip. If desired, ribs 33 may be located on opposed surfaces of each handle. The handle 29 has the same structure.

Figure 6:
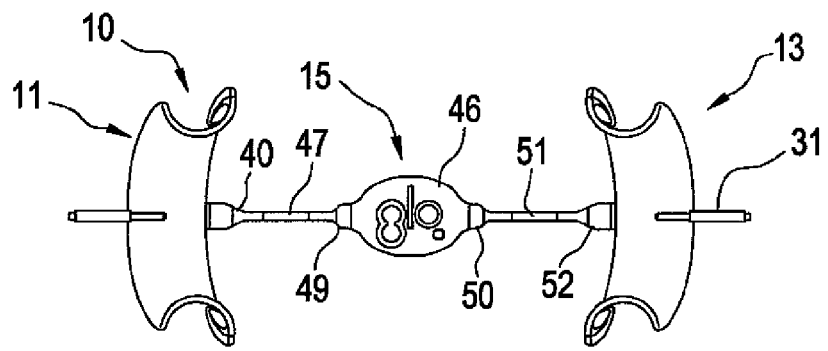
FIG. 6 shows a view similar to that of FIG. 5 but with the trays rotated from the orientation shown in FIG. 5.
Figure 7:
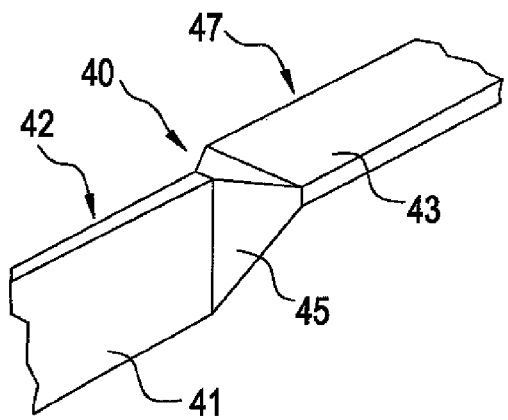
FIG. 7 shows a close-up perspective view of a portion of the strap-like member of the present invention.
Figure 8:
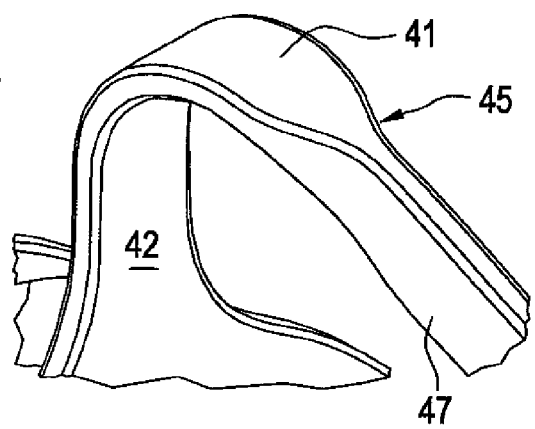
FIG. 8 shows a close-up view of a portion of the strap-like member of the present invention where it transitions from one of the trays thereof.

FIGS. 1, 4, 5, 7 and 8 in particular show details of certain aspects of the strap-like member 15 which includes (FIG. 1) first and fifth flat portions 42 and 44, respectively, connected by second 47, third 46 and fourth 51 flat portions. Thus, FIG. 7 shows an enlarged view of a thickened first transition location or area identified by the reference numeral 40 in FIG. 5. The transition transitions the strap-like member from a first orientation 41 of the strap 42 to an orientation 90° rotated from the orientation of the first orientation 41 and designated by the reference numeral 43 of the flat portion 47. The transition area 45 is a thickened area that accommodates the transition. This is further shown with reference to FIG. 8. The elongated cross-section of said third flat portion 46 is elongated in a direction perpendicular to a direction of elongation of said cross-sections of said first and second flat portions. The third flat portion 46 has a central widened oval-shaped portion 48 (FIG. 1). As also seen in these figures, a second transition area 49 is between the flat portions 47 and 46 and transitions the strap so the flat portions 47 and 46 are angularly displaced with respect to one another. Similarly, a third transition area 50 transitions the strap between the flat portions 46 and 51 so that they are angularly displaced with respect to one another. Similarly, a fourth transition area 52 transitions the strap between the flat portions 51 and 44 so that they are angularly displaced with respect to one another.

With reference to FIG. 4, it is seen that in the relaxed position of the retractor 10, the walls 19 (of the tray 11) and 25 (of the tray 13) subtend an angle of approximately 30°. This angulation improves the comfort level of the patient because it is more closely and effectively aligned with the anatomy of a human oral cavity. In addition, the height of the walls 17, 19, 23 and 25 is specifically devised to improve the fit of the retractor 10 and also to preclude the lips of the user from slipping out of the surfaces 21 and 27.

In use, the inventive retractor is inserted into the mouth of the user as shown in FIG. 11 with the trays 11 and 13 located on the sides of the lips of the user and with the strap-like member 15 between the bite surfaces of the upper and lower teeth of the user. In that position and orientation, a teeth whitening substance may be painted or otherwise coated onto the visible surfaces of the teeth without coating the lips or gums of the user.

Thereafter, a mouthpiece may be inserted into the mouth covering the user's teeth and enclosing and sealing in the teeth whitening substance so that oxygen molecules may not escape during the whitening procedure.

In one preferred method of use of the inventive retractor 10, the mouthpiece employed is as sold by Glo Science, Inc. and disclosed and claimed in U.S. patents including U.S. Pat. No. 8,371,853 issued Feb. 12, 2013. That device includes an electrical circuit embedded within the mouthpiece that has blue light LEDs and heat generators to allow light and heat to enhance the whitening process.

Of course, the present invention may be practiced with any desired mouthpiece or even without a mouthpiece as desired.

The inventive retractor is preferably made of a flexible material such as rubber, synthetic rubber or soft plastic to enhance the comfort level of the patient when the retractor is being used. The retractor may be manufactured by injection molding, pressure molding, or any other desired manufacturing technique.

As such, an invention has been disclosed in terms of a preferred embodiment thereof which fulfills each and every one of the objects of the invention as set forth hereinabove, and provides a new and useful dental retractor for use in teeth whitening of great novelty and utility.

Of course, various changes, modifications and alterations in the teachings of the present invention may be contemplated by those of ordinary skill in the art without departing from the intended spirit and scope thereof.

As such, it is intended that the present invention only be limited by the terms of the appended claims.

The invention claimed is:

1. A dental retractor, comprising:
   a) first and second arcuate trays interconnected by an elongated strap;
   b) each tray including a surface with a generally U-shaped cross-section, each said surface shaped to engage a side of a user's mouth, including intersecting portions of a user's upper and lower lips; and
   c) said strap including a flat cross-section including, from said first tray to said second tray, a first flat portion emanating from said first arcuate tray, a first transition area transitioning said strap, a second flat portion rotated with respect to said first flat portion, a second transition area transitioning said strap, a third flat portion rotated with respect to said second flat portion, a third transition area transitioning said strap, a fourth flat portion rotated with respect to said third flat portion, a fourth transition area transitioning said strap, and a fifth flat portion rotated with respect to said fourth flat portion, said fifth flat portion connected to said second arcuate tray, wherein the first transition area is thickened with respect to the first flat portion and the second flat portion.

2. The dental retractor of claim 1, wherein each tray has a handle connected thereto.

3. The dental retractor of claim 2, wherein each handle is formed integrally with a respective one of said first and second arcuate trays.

4. The dental retractor of claim 3, wherein each handle includes a gripping surface thereon.

5. The dental retractor of claim 4, wherein said gripping surface comprises a plurality of raised ribs.

6. The dental retractor of claim 2, wherein each handle includes a gripping surface thereon.

7. The dental retractor of claim 6, wherein said gripping surface comprises a plurality of raised ribs.

8. The dental retractor of claim 7, wherein each handle is located on an outside wall of a respective one of said first and second arcuate trays.

9. The dental retractor of claim 2, wherein each handle is located on an outside wall of a respective one of said first and second arcuate trays.

10. The dental retractor of claim 1, wherein each said flat portion has an elongated cross-section in a direction perpendicular to a direction of extension thereof.

11. The dental retractor of claim 10, wherein said elongated cross-section of said third flat portion is elongated in a direction perpendicular to a direction of elongation of said cross-sections of said second and fourth flat portions.

12. The dental retractor of claim 11, wherein a center portion of said third flat portion is widened and oval-shaped.

13. The dental retractor of claim 12, wherein said third flat portion is configured to be gripped between a user's upper and lower teeth.

14. The dental retractor of claim 11, wherein said second transition area is thickened between said second and third flat portions.

15. The dental retractor of claim 14, further wherein said third transition area is thickened between said third and fourth flat portions.

16. The dental retractor of claim 1, made of a material chosen from the group consisting of rubber, synthetic rubber, and plastic.

17. A dental retractor, comprising:
 a) first and second arcuate trays interconnected by an elongated strap;
 b) each tray including a surface with a generally U-shaped cross-section, each said surface shaped to engage a side of a user's mouth, including intersecting portions of a user's upper and lower lips; and
 c) said strap including a flat cross-section including, from said first tray to said second tray, a first flat portion emanating from said first arcuate tray, a first transition area transitioning said strap, a second flat portion rotated with respect to said first flat portion, a second transition area transitioning said strap, a third flat portion rotated with respect to said second flat portion, a third transition area transitioning said strap, a fourth flat portion rotated with respect to said third flat portion, a fourth transition area transitioning said strap, and a fifth flat portion rotated with respect to said fourth flat portion, said fifth flat portion connected to said second arcuate tray, wherein the first transition area is thickened with respect to the first flat portion and the second flat portion;
 d) each tray having a handle integrally connected thereto to an outside wall thereof; and e) further wherein each said flat portion has an elongated cross-section in a direction perpendicular to a direction of extension thereof.

18. The dental retractor of claim 17, wherein each handle includes a gripping surface thereon comprising a plurality of raised ribs.

19. The dental retractor of claim 17, wherein said elongated cross-section of said third flat portion is elongated in a direction perpendicular to a direction of elongation of said cross-sections of said second and fourth flat portions, and a center portion of said third flat portion is widened and oval-shaped.

20. The dental retractor of claim 17, made of a material chosen from the group consisting of rubber, synthetic rubber, and plastic.

\* \* \* \* \*